(12) United States Patent
Carini

(10) Patent No.: US 6,943,170 B2
(45) Date of Patent: Sep. 13, 2005

(54) N-CYCLOALKYLGLYCINES AS HIV PROTEASE INHIBITORS

(75) Inventor: David J. Carini, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 145 days.

(21) Appl. No.: 10/697,807

(22) Filed: Oct. 30, 2003

(65) Prior Publication Data

US 2004/0142878 A1 Jul. 22, 2004

Related U.S. Application Data

(60) Provisional application No. 60/426,224, filed on Nov. 14, 2002.

(51) Int. Cl.⁷ ..................... C07C 311/16; C07D 239/24; C07D 237/06; A61K 31/18; A61P 31/18

(52) U.S. Cl. ............... 514/256; 514/252.1; 514/252.01; 514/336; 514/357; 514/603; 514/601; 514/602; 514/312; 514/351; 514/367; 514/412; 544/242; 544/333; 544/224; 544/238; 544/336; 544/405; 544/354; 546/268.1; 546/329; 546/153; 548/165; 548/361.5; 564/86

(58) Field of Search .................. 564/86; 546/268.1, 546/329; 544/242, 333, 224, 238, 336, 405; 514/603, 336, 357, 256, 252.01

(56) References Cited

U.S. PATENT DOCUMENTS

| 5,756,533 | A | 5/1998 | Getman et al. |
|---|---|---|---|
| 5,776,971 | A | 7/1998 | Getman et al. |
| 6,046,190 | A | 4/2000 | Vazquez et al. |
| 6,143,788 | A | 11/2000 | Getman et al. |
| 6,150,556 | A | 11/2000 | Getman et al. |
| 6,156,768 | A | 12/2000 | Vazquez et al. |
| 6,391,919 | B1 | 5/2002 | Kaltenbach et al. |

*Primary Examiner*—Venkataraman Balasubramanian
(74) *Attorney, Agent, or Firm*—James Epperson; Scott K. Larsen

(57) ABSTRACT

This invention relates generally to N-cycloalkylglycines of the Formula (I):

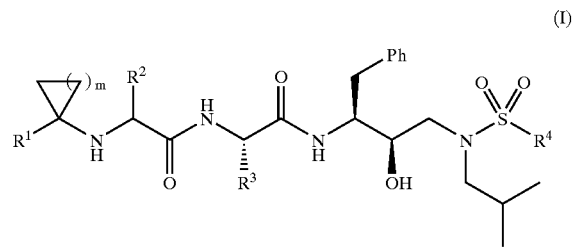

(I)

or a stereoisomeric form, a mixture of stereoisomeric forms, or a pharmaceutically acceptable salt thereof, which are useful as HIV protease inhibitors, pharmaceutical compositions and diagnostic kits including the same, methods for using the same for treating viral infection or an assay standards or reagents, and intermediates and processes for making the same.

15 Claims, No Drawings

N-CYCLOALKYLGLYCINES AS HIV PROTEASE INHIBITORS

REFERENCE TO RELATED APPLICATIONS

This application claims the benefit of U.S. Provisional Application Ser. No. 60/426,224 filed Nov. 14, 2002.

FIELD OF THE INVENTION

This invention relates generally to N-cycloalkylglycines useful as HIV protease inhibitors, pharmaceutical compositions and diagnostic kits including the same, and methods for using the same for treating viral infection or an assay standards or reagents.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression, which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

The genomes of retroviruses encode a protease that is responsible for the proteolytic processing of one or more polyprotein precursors such as the pol and gag gene products. See Willink, Arch. Virol. 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., J. Virol. 53 899 (1985); Katoh et al., Virology 145 280 (1985). Therefore, retroviral protease inhibition provides an attractive target for antiviral therapy. See Mitsuya, Nature 325 775 (1987).

As evidenced by the protease inhibitors presently marketed and in clinical trials, a wide variety of compounds have been studied as potential HIV protease inhibitors. Hydroxyethylamino-sulfonamides have been disclosed in the literature. See, for example, Kaltenbach and Trainor U.S. Pat. No. 6,391,919, 2002; Vazquez et al. U.S. Pat. No. 6,156,768, 2000; Getman et al. U.S. Pat. No. 6,150,556, 2000; Getman et al. U.S. Pat. No. 6,143,788, 2000; Vazquez et al. U.S. Pat. No. 6,046,190, 2000; Getman et al. U.S. Pat. No. 5,776,971, 1998; and Getman et al. U.S. Pat. No. 5,756,533, 1998. These disclosures do not teach or suggest the compounds of this invention.

SUMMARY OF THE INVENTION

Accordingly, one object of the present invention is to provide novel protease inhibitors.

It is another object of the present invention to provide a novel method for treating HIV infection which comprises administering to a host in need of such treatment a therapeutically effective amount of at least one of the compounds of the present invention or a pharmaceutically acceptable salt form thereof.

It is another object of the present invention to provide a novel method for treating HIV infection which comprises administering to a host in need thereof a therapeutically effective combination of (a) one of the compounds of the present invention and (b) another therapeutic agent (e.g., one or more compounds selected form the group HIV reverse transcriptase inhibitors and HIV protease inhibitors).

It is another object of the present invention to provide pharmaceutical compositions with protease inhibiting activity comprising a pharmaceutically acceptable carrier and a therapeutically effective amount of at least one of the compounds of the present invention or a pharmaceutically acceptable salt form thereof.

It is another object of the present invention to provide a method of inhibiting HIV present in a body fluid sample, which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV protease, HIV growth, or both.

These and other objects, which will become apparent during the following detailed description, have been achieved by the inventors' discovery that compounds of Formula (I) or pharmaceutically acceptable salts thereof

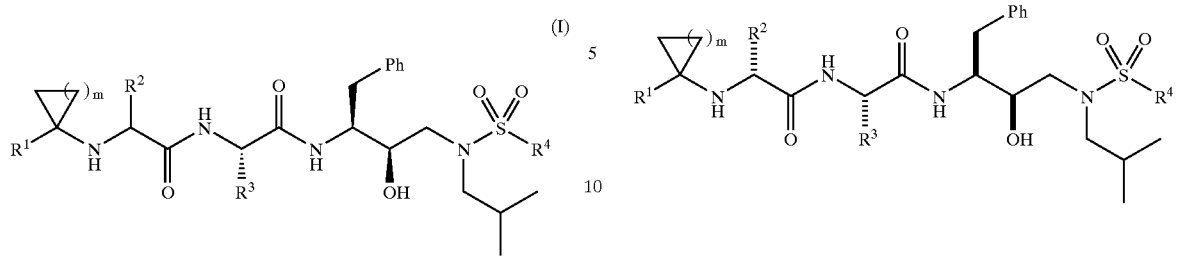

wherein:

- $R^1$ is phenyl, pyridinyl, pyrimidinyl, pyrazinyl, or pyridazinyl, and is unsubstituted or substituted with 1-2 substituents selected from the group consisting of halogen, $C_{1-6}$alkyl, trifluoromethyl, $C_{1-6}$alkoxy, trifluoromethoxy, and cyano;
- $R^2$ is hydrogen or $C_{1-6}$alkyl;
- $R^3$ is selected from the group consisting of isopropyl, tert-butyl, sec-butyl, and $C(CH_3)_2SCH_3$;
- $R^4$ is phenyl, indazolyl, benzothiazolyl, quinolinyl, quinoxalinyl, 2,3-dihydrobenzofuranyl, or 1,3-benzodioxolyl, and is unsubstituted or substituted with 1-2 substituents selected from the group consisting of amino, acetamido, halo, $C_{1-6}$alkyl, trifluoromethyl, $C_{1-6}$alkoxy, trifluoromethoxy, and cyano; and
- m is 1, 2, 3, or 4;

are effective protease inhibitors; inhibit HIV protease, HIV growth, or both.

In another embodiment, the invention provides compounds of Formula I wherein $R^1$ is phenyl, 3-fluorophenyl, 4-fluorophenyl, 3,5-difluorophenyl, 2,4-difluorophenyl, 2,6-difluorophenyl, 3-trifluoromethylphenyl, 3-pyridinyl, or 3-methoxyphenyl.

In another embodiment, the invention provides compounds of Formula I where $R^1$ is phenyl, 3-fluorophenyl, 4-fluorophenyl, 3,5-difluorophenyl, 3-trifluoromethylphenyl, 3-pyridinyl, or 3-methoxyphenyl.

In another embodiment, the invention provides compounds of Formula I where $R^2$ is hydrogen or methyl.

In another embodiment, the invention provides compounds of Formula I where $R^4$ is selected from the group consisting of 4-aminophenyl, 3-aminophenyl, 3-amino-4-methylphenyl, 4-methoxyphenyl, 6-benzothiazolyl, 2-amino-6-benzothiazolyl, 2-acetamido-6-benzothiazolyl, 2-methyl-6-benzothiazolyl, 7-benzothiazolyl, 2-amino-7-benzothiazolyl, 2-acetamido-7-benzothiazolyl, 2-methyl-7-benzothiazolyl, 2,3-dihydrobenzofuran-5-yl, 2,3-benzodioxl-5-yl, 6-indazolyl, 6-quinolinyl, and 6-quinoxalinyl.

In another embodiment, the invention provides compounds of Formula I where $R^4$ is selected from the group consisting of 4-aminophenyl, 3-amino-4-methylphenyl, 6-indazolyl, 6-benzothiazolyl, 2-methyl-6-benzothiazolyl, 2-amino-6-benzothiazolyl, 6-quinolinyl, and 6-quinoxalinyl.

In another embodiment, the invention provides compounds of Formula I with the stereochemistry as designated in Formula Ia.

In another embodiment, the invention provides compounds of Formula I where m is 1.

Some compounds of the invention include the following:

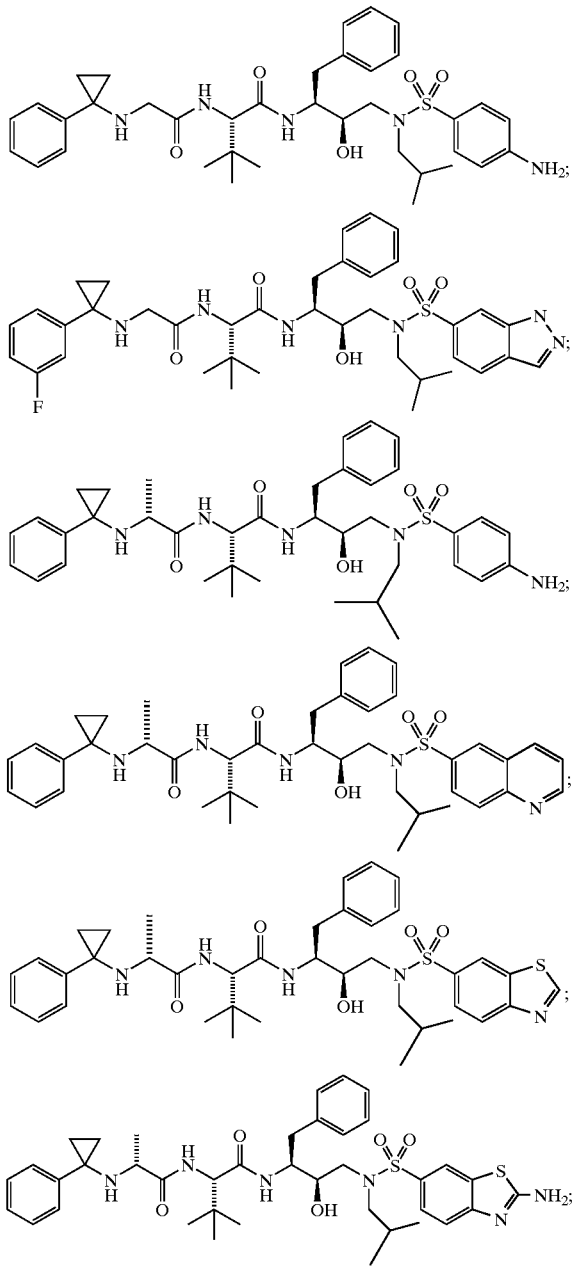

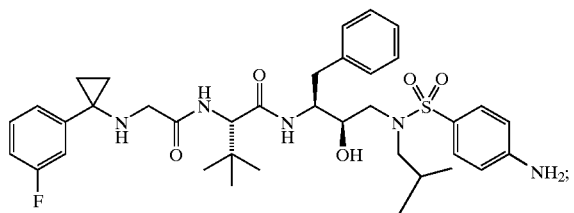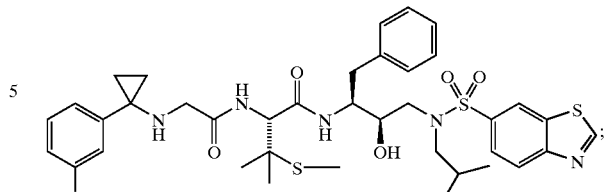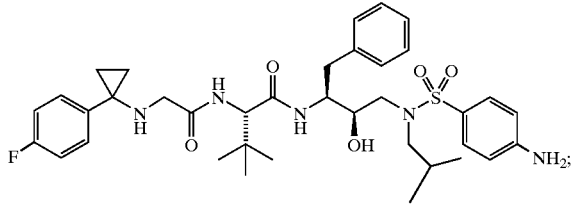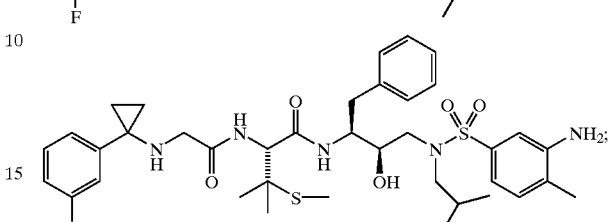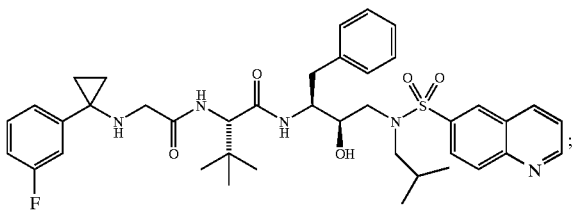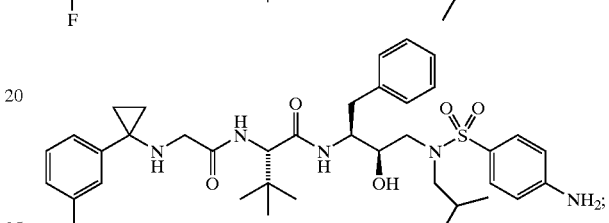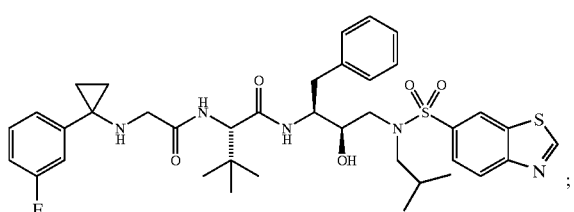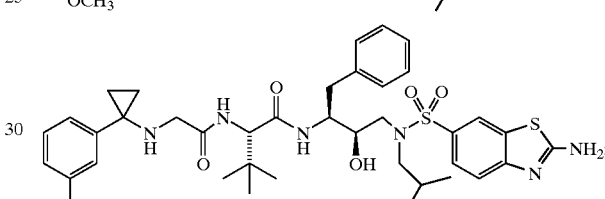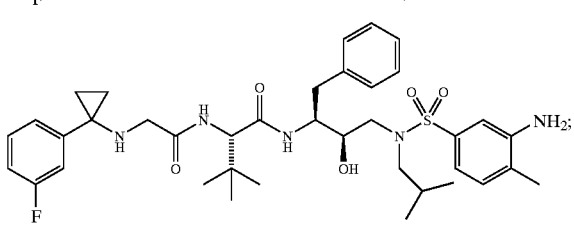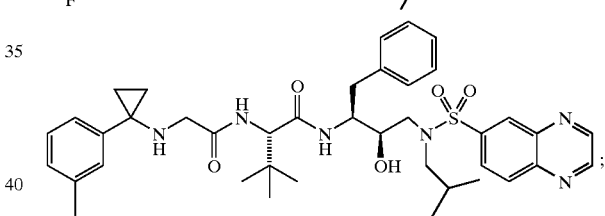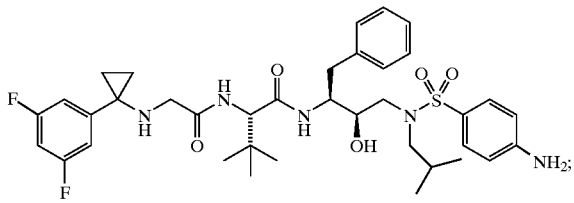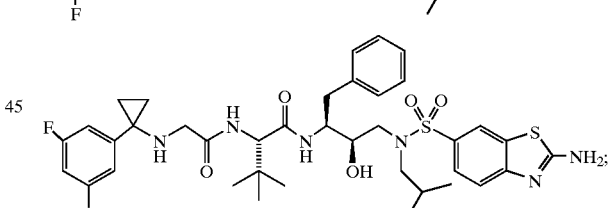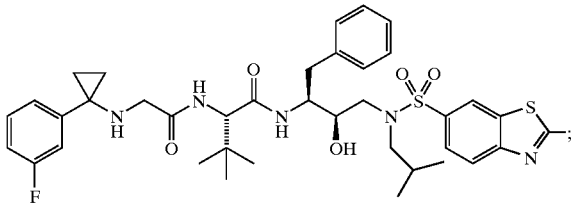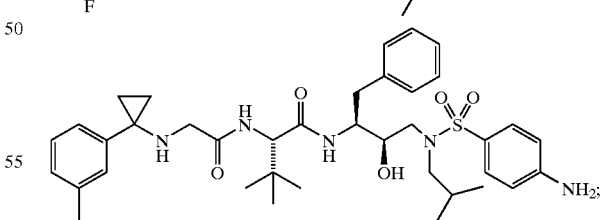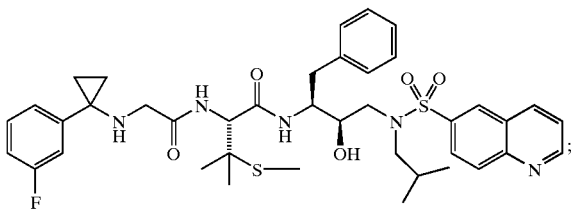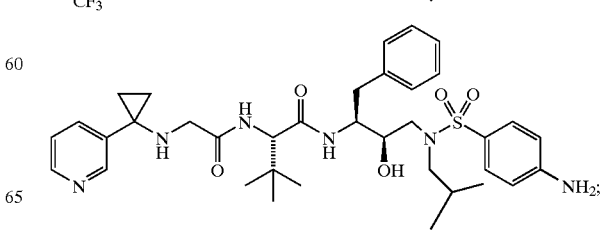

-continued

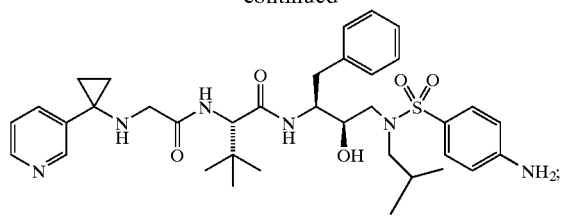

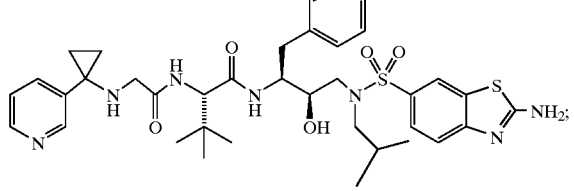

and

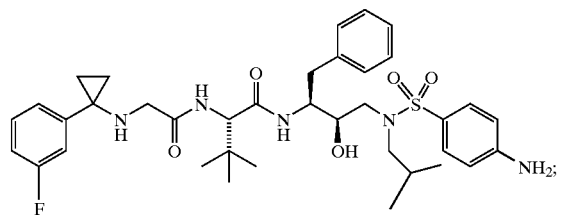

and pharmaceutically acceptable salts thereof.

In another embodiment, the present invention provides a novel pharmaceutical composition comprising a pharmaceutically acceptable carrier and a therapeutically effective amount of a compound of Formula (I) or pharmaceutically acceptable salt form thereof.

In another embodiment, the present invention provides a novel method for treating HIV infection which comprises administering to a host in need of such treatment a therapeutically effective amount of a compound of Formula (I) or stereoisomeric forms, mixtures of stereoisomeric forms, or pharmaceutically acceptable salts thereof.

In another embodiment, the present invention provides a novel method of treating HIV infection which comprises administering, in combination, to a host in need thereof a therapeutically effective amount of:

(a) a compound of Formula (I); and,
(b) at least one compound selected from the group HIV reverse transcriptase inhibitors and HIV protease inhibitors.

In another embodiment, the reverse transcriptase inhibitor is selected from the group AZT, ddC, ddI, d4T, 3TC, delavirdine, efavirenz, nevirapine, Ro 18, 893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In another embodiment, the reverse transcriptase inhibitor is selected from the group AZT, efavirenz, and 3TC and the protease inhibitor is selected from the group saquinavir, ritonavir, nelfinavir, and indinavir.

In another embodiment, the reverse transcriptase inhibitor is AZT.

In another embodiment, the protease inhibitor is indinavir.

In another, component (b) is a HIV reverse transcriptase inhibitor and a HIV protease inhibitor.

In another embodiment, component (b) is two different HIV reverse transcriptase inhibitors.

In another embodiment, the present invention provides a pharmaceutical composition useful for the treatment of HIV infection, which comprises a therapeutically effective amount of:

(a) a compound of Formula (I); and,
(b) at least one compound selected from the group HIV reverse transcriptase inhibitors and HIV protease inhibitors, in one or more sterile containers.

In another embodiment, the present invention provides a novel method of inhibiting HIV present in a body fluid sample which comprises treating the body fluid sample with an effective amount of a compound of Formula (I).

In another embodiment, the present invention provides a novel kit or container comprising a compound of Formula (I) in an amount effective for use as a standard or reagent in a test or assay for determining the ability of a potential pharmaceutical to inhibit HIV protease, HIV growth, or both.

In another embodiment, the present invention provides a compound of Formula (I) for use in medical therapy.

In another embodiment, the present invention provides the use of a compound of Formula (I) for the manufacture of a medicament for treating HIV infection.

DETAILED DESCRIPTION OF THE INVENTION

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomeric form is specifically indicated. With the center bearing $R^2$, this center can be either (R)- or (S)- or a mixture of the two.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Example of non-nucleoside RT inhibitors include, but are not limited to, delavirdine (Pharmacia and Upjohn, U90152S), efavirenz (Bristol-Myers Squibb), nevirapine (Boehringer Ingelheim), Ro 18,893 (Roche), trovirdine (Lilly), MKC-442 (Triangle), HBY 097 (Hoeschst), HBY 1293 (Hoeschst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds which inhibits HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), tipranavir (Pharmacia and Upjohn, U-140690), DMP-450 (Bristol-Myers Squibb) and ABT-378.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more (e.g., 1, 2, 3, 4, or 5; preferably 1, 2, or 3; and more preferably 1 or 2) hydrogens on the group indicated in the expression using "substituted" is replaced with a selection from the indicated group(s), provided that the indicated atom's normal valency is not exceeded, and that the substitution results in a stable compound. For example, "substituted aryl" is intended to mean an "aryl" group substituted by one or more (e.g., 1, 2, 3, 4, or 5; preferably 1, 2, or 3; and more preferably 1 or 2) indicated group(s). When a substituent is keto (i.e., =O) or thioxo (i.e., =S) group, then 2 hydrogens on an atom of the indicated group are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

One diastereomer of a compound of Formula (I) may display superior activity compared with the other. When required, separation of the racemic material can be achieved by HPLC using a chiral column or by a resolution using a resolving agent such as camphonic chloride as in Thomas J. Tucker, et al., *J. Med. Chem.* 1994 37, 2437–2444. A chiral compound of Formula (I) may also be directly synthesized using a chiral catalyst or a chiral ligand, e.g. Mark A. Huffman, et al., *J. Org. Chem.* 1995, 60, 1590–1594.

The term "alkyl" refers to a monoradical branched or unbranched saturated hydrocarbon chain preferably having 1, 2, 3, 4, 5, or 6 carbon atoms, and more preferably from 1, 2, 3, or 4 carbon atoms. Examples of alkyl include, but are not limited to, methyl, ethyl, n-propyl, iso-propyl, n-butyl, iso-butyl, sec-butyl, n-hexyl, and the like. Preferred "alkyl" group, unless otherwise specified, is methyl, ethyl, n-propyl, iso-propyl, n-butyl, iso-butyl, and sec-butyl.

The term "substituted alkyl" refers to an "alkyl" group which is substituted, for example, with one or more (preferably 1, 2, 3, 4, or 5; more preferably 1, 2, or 3) substituents, independently selected from methyl, ethyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, dialkylsulfonamido, aryl, substituted aryl, heteroaryl, substituted heteroaryl, heterocycle, substituted heterocycle, cycloalkyl, substituted cycloalkyl, keto, and thioxo.

The term "alkenyl", as used herein, is intended to include monoradical hydrocarbon chains of either a straight or branched configuration and one or more unsaturated carbon-carbon bonds which may occur in any stable point along the chain preferably having 2, 3, 4, 5, or 6 carbon atoms, more preferably from 2, 3, or 4 carbon atoms. This term is exemplified by groups such as ethenyl, 1-propenyl, 2-propenyl, 1-butenyl, 2-butenyl, 3-butenyl, 1-hexenyl, 2-hexenyl, 3-hexenyl, and the like.

The term "alkynyl" refers to a monoradical hydrocarbon chain of either a straight or branched configuration and one or more carbon-carbon triple bonds which may occur in any stable point along the chain, preferably having from 2, 3, 4, 5, or 6 carbon atoms, and more preferably from 2, 3 or 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. Preferred alkoxy groups are methoxy, ethoxy, n-propoxy, i-propoxy, n-butoxy, s-butoxy, and t-butoxy.

The term "aryl" refers to an unsaturated aromatic carbocyclic group of from 6 to 12 carbon atoms having a single ring (e.g., phenyl) or multiple condensed (fused) rings, wherein at least one ring is aromatic (e.g., naphthyl, tetrahydronaphthyl, dihydrophenanthrenyl, fluorenyl, or anthryl). Preferred aryls include phenyl, naphthyl and the like.

The term "substituted aryl" refers to an "aryl" group which is substituted, for example, with one or more, and in particular one to three, substituents, independently selected from methyl, ethyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, and dialkylsulfonamido.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclohexyl, cycloheptyl, cyclooctyl, and the like, or multiple ring structures such as adamantanyl, and the like. Preferred cycloalkyl groups include cyclopropyl, cyclobutyl, cyclopentyl, and cyclohexyl.

The term "substituted cycloalkyl" refers to a "cycloalkyl" group which is substituted, for example, with one or more, and in particular 1, 2, or 3, substituents, independently selected from alkyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, dialkylsulfonamido, keto, and thioxo.

The term "halo" or "halogen" refers to fluoro, chloro, bromo, or iodo. Unless otherwise specified, preferred halo is fluoro or chloro.

"Haloalkyl" refers to alkyl as defined herein substituted by 1, 2, 3, 4, or 5 halo groups as defined herein, which may be the same or different. Representative haloalkyl groups include, by way of example, difluoromethyl, trifluoromethyl, trichloromethyl, pentafluoroethyl, pentachloroethyl, 2,2,2-trifluoroethyl, 2,2-difluoroethyl, and the like. Preferred haloalkyl is selected from difluoromethyl and trifluoromethyl.

The term "heteroaryl" is defined herein as a monocyclic, bicyclic, or tricyclic ring system containing one, two, or three aromatic rings and containing at least one nitrogen, oxygen, or sulfur atom in an aromatic ring.

Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group nonperoxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "substituted heteroaryl" is defined herein as a "heteroaryl" group which is substituted, for example, with one or more, and in particular 1, 2, or 3, substituents, independently selected from alkyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, and dialkylsulfonamido.

The term "heterocycle" refers to a saturated or partially unsaturated ring system, containing at least one heteroatom selected from the group oxygen, nitrogen, and sulfur. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "substituted heterocycle" refers to a "heterocycle" group, as defined herein, which is substituted with one or more, and in particular one to three, substituents, selected from alkyl, alkenyl, alkynyl, alkoxy, halo, haloalkyl, hydroxy, hydroxyalkyl, aryl, heteroaryl, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl and cyano.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Preferred 5 to 6 membered heterocycles include, but are not limited to, pyridinyl, pyrimidinyl, pyrazinyl, pyridazinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl.

The term "alkanoyl" refers to $-C(=O)R^a$, wherein $R^a$ is an alkyl group as previously defined.

The term "alkoxycarbonyl" refers to $-C(=O)OR^a$, wherein $R^a$ is an alkyl group as previously defined.

The term "amino" refers to —NH$_2$.

The term "alkylamino" refers to —NHR$^a$, wherein R$^a$ is an alkyl group as previously defined.

The term "dialkylamino" refers to —N(R$^a$)$_2$ wherein each R$^a$ is an alkyl group as previously defined and may be the same or different.

The term "amido" refers to —C(=O)NH$_2$.

The term "alkylamido" refers to —C(=O)NHR$^a$, wherein R$^a$ is an alkyl group as previously defined.

The term "dialkylamido" refers to —C(=O)N(R$^a$)$_2$ wherein each R$^a$ is an alkyl group as previously defined and may be the same or different.

The term "acylamino" refers to —NHC(=O)R$^b$, wherein R$^b$ is an alkyl group or an aryl group as previously defined.

The term "sulfonylamino" refers to —NHS(=O)$_2$R$^b$, wherein R$^b$ is an alkyl group or an aryl group as previously defined.

The term "alkylthio" refers to the groups alkyl-S—, wherein alkyl is as previously defined herein.

The term "alkylsulfinyl" refers to —S(=O)R$^a$, wherein R$^a$ is an alkyl group as previously defined.

The term "alkylsulfonyl" refers to —S(=O)$_2$R$^a$, wherein R$^a$ is an alkyl group as previously defined.

The term "sulfonamido" refers to —S(=O)$_2$NH$_2$.

The term "alkylsulfonamido" refers to —S(=O)$_2$NHR$^a$, wherein R$^a$ is an alkyl group as previously defined.

The term "dialkylsulfonamido" refers to —S(=O)$_2$N(R$^a$)$_2$ wherein each R$^a$ is an alkyl group as previously defined and may be the same or different.

The term "nitro" refers to —NO$_2$.

The term "difluoromethyl" refers to —CHF$_2$.

The term "trifluoromethyl" refers to —CF$_3$.

The term "trifluoromethoxy" refers to —OCF$_3$.

The term "trifluoromethylthio" refers to —SCF$_3$.

The term "cyano" refers to —CN.

The term "hydroxy" refers to —OH.

The term "hydroxyalkyl" refers to an alkyl group as defined above substituted by a hydroxy group.

The term "carboxyalkyl" refers to an alkyl group as defined above substituted by a —CO$_2$H group.

The term "carboxy" refers to —CO$_2$H.

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Other features of the invention will become apparent in the course of the following descriptions of exemplary embodiments which are given for illustration of the invention and are not intended to be limiting thereof.

As used herein, "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis Mo.

Utility

The compounds of Formula (I) possess HIV protease inhibitory activity and are therefore useful as antiviral agents for the treatment of HIV infection and associated diseases. The compounds of Formula (I) possess HIV protease inhibitory activity and are effective as inhibitors of HIV growth. The ability of the compounds of the present invention to inhibit viral growth or infectivity is demonstrated in standard assay of viral growth or infectivity, for example, using the assay described below.

The compounds of Formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV protease, for example in a pharmaceutical research program. Thus, the compounds of the present invention may be used as control or reference compound in such assays and as a quality control standard. The compounds of the present invention may be provided in a commercial kit or container for use as such standard or reference compound.

Since the compounds of the present invention exhibit specificity for HIV protease, the compounds of the present invention may also be useful as diagnostic reagents in diagnostic assays for the detection of HIV protease. Thus, inhibition of the protease activity in an assay (such as the assays described herein) by a compound of the present invention would be indicative of the presence of HIV protease and HIV virus.

HIV RNA Assay

DNA Plasmids and In Vitro RNA Transcripts:

Plasmid PDAB 72 containing both gag and pol sequences of BH10 (bp 113-1816) cloned into PTZ 19R was prepared according to Erickson-Vitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70EC. The concentration of RNA was determined from the A$_{260}$.

Probes:

Biotinylated capture probes were purified by HPLC after synthesis on an Applied Biosystems (Foster city, Calif.) DNA synthesizer by addition of biotin to the 5N terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTT GCCCATACTA 3N) was complementary to nucleotides 889–912 of HXB2 and the pol biotinylated capture probe (5N-biotin -CCCTATCATTTTTGGTTTCCAT 3N) was complementary to nucleotides 2374–2395 of HXB2. Alkaline phosphatase conjugated oligonucleotides used as reporter probes were prepared by Syngene (San Diego, Calif.). The pol reporter probe (5N CTGTCT-TACTTTGATAAAACCTC 3N) was complementary to nucleotides 2403–2425 of HXB2. The gag reporter probe (5N CCCAGTATTTGTCTACAGCCTTCT 3N) was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 :M stocks in 2×SSC (0.3 M NaCl, 0.03 M sodium citrate), 0.05 M Tris pH 8.8, 1 mg/mL BSA. The biotinylated capture probes were prepared as 100 M stocks in water.

Streptavidin Coated Plates:

Streptavidin coated plates were obtained from Du Pont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1 (RF) stocks were 1–3×10$^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection, On the day of infection, cells were resuspended at 5×10$^5$ cells/mL in RPMI 1640, 5% FCS for bulk infections or at 2×10$^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline (PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton× 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer δ (2.5 M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nN.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of 5×10$^5$ per mL (1×10$^5$ per well). Cells were incubated with compounds for 30 minutes at 37° C. in a CO$_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a CO$_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nN capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an IC$_{90}$ value (concentration of compound required to reduce the HIV RNA level by 90%) for dideoxycytidine (ddC) of 0.2 µg/mL. IC$_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, IC$_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The IC$_{90}$ for ddC, determined in each assay run, should be between 0.1 and 0.3 µg/mL. Finally, the plateau level of viral RNA produced by an effective protease inhibitor should be less than 10% of the level achieved in an uninhibited infection. A compound was considered active if its IC$_{90}$ was found to be less than 1 µM. Compounds of the invention have demonstrated IC$_{90}$ of less than 1 µM in the above assay. For antiviral potency tests, all manipulations in microtiter plates, following the initial addition of 2× concentrated compound solution to a single row of wells, were performed using a Perkin Elmer/Cetus ProPette.

In addition to the above, it is desirable to find new compounds with improved pharmacological characteristics compared with known HIV protease inhibitors. For example, it is preferred to find new compounds with improved HIV protease inhibitory activity and selectivity for HIV protease versus other enzymes. It is also desirable and preferable to find compounds with advantageous and improved characteristics in one or more of the following categories:

(a) pharmaceutical properties (i.e. solubility, permeability, amenability to sustained release formulations);

(b) dosage requirements (e.g., lower dosages and/or once-daily dosing);

(c) factors which decrease blood concentration peak-to-trough characteristics (i.e. clearance and/or volume of distribution);

(d) factors that increase the concentration of active drug at the receptor (i.e. protein binding, volume of distribution);

(e) factors that decrease the liability for clinical drug-drug interactions (cytochrome P450 enzyme inhibition or induction);

(f) factors that decrease the potential for adverse side-effects (i.e. pharmacological selectivity beyond HIV proteases, potential chemical or metabolic reactivity, limited CNS penetration); and (g) factors that improve manufacturing costs or feasibility (i.e. difficulty of synthesis, number of chiral centers, chemical stability, ease of handling).

Dosage and Formulation

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 1000 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 1000 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 1000 mg of the active ingredient. The capsules should then be washed and dried.

Tablets

A large number of tablets can be prepared by conventional procedures so that the dosage unit is 1000 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently. Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds, which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Synthesis

Abbreviations used in the Examples are defined as follows: "atm" for atmosphere, "br s" for broad singlet, "° C." for degrees Celsius, "d" for doublet, "eq" for equivalent or equivalents, "g" for gram or grams, "mg" for milligram or milligrams, "mL" for milliliter or milliliters, "H" for hydrogen or hydrogens, "HPLC" for high-pressure liquid chromatography, "m" for multiplet, "mmol" for millimole or millimoles, "hr" for hour or hours, "m" for multiplet, "M" for molar, "min" for minute or minutes, "MHz" for megahertz, "MS" for mass spectroscopy, "N" for normal, "nmr" or "NMR" for nuclear magnetic resonance spectroscopy, "s" for singlet, "t" for triplet, and "TLC" for thin layer chromatography.

EXAMPLE 1

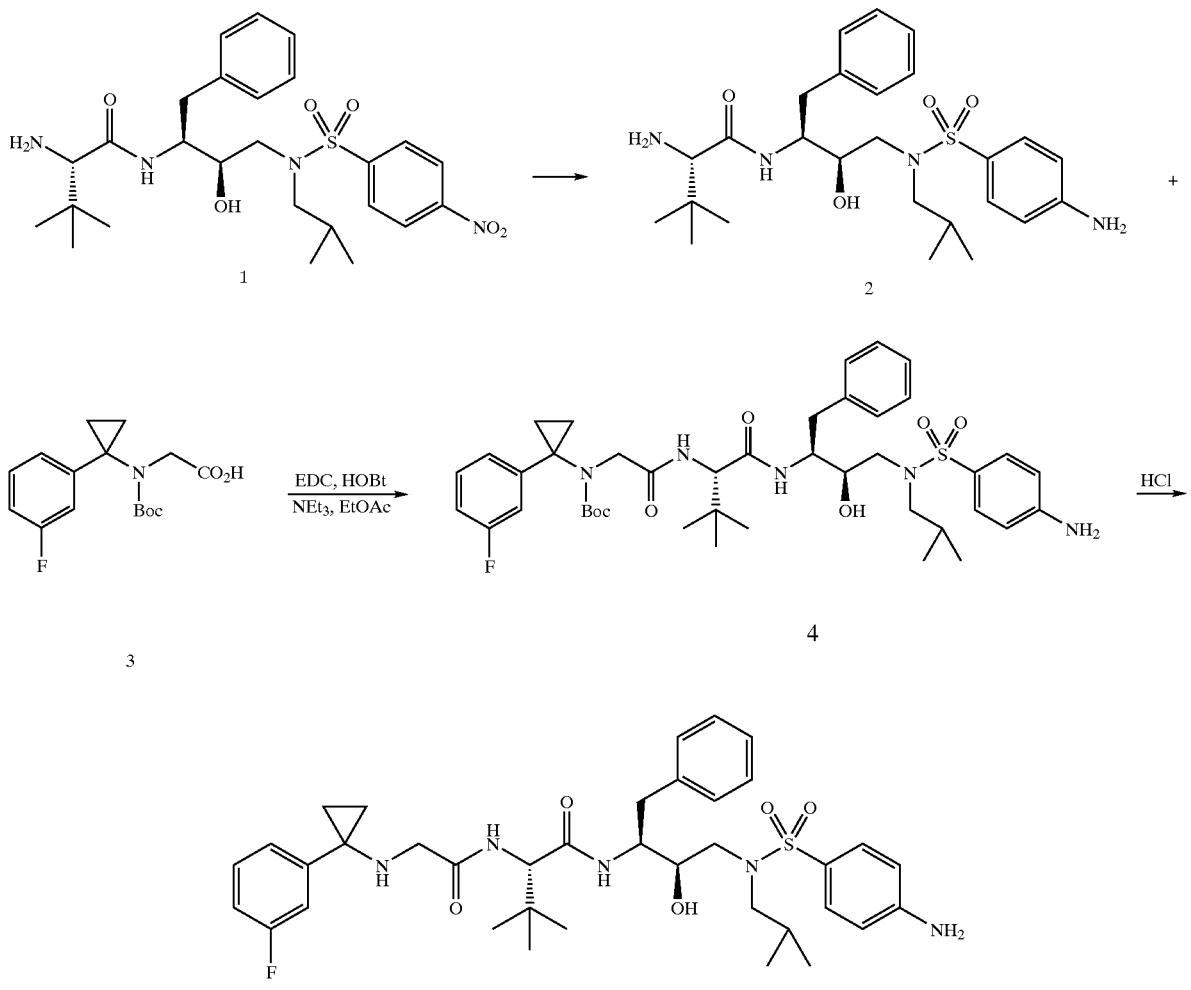

Example 1

Step 1: A solution of 6.3 g (10 mmol) of 1 in water was made basic by the addition of 1 N aqueous sodium hydroxide solution, and the resulting mixture was extracted with ethyl acetate. The extract was washed with brine, dried over anhydrous sodium sulfate, filtered, and concentrated. The residue was dissolved in 50 mL of ethyl acetate and 50 mL of methanol. This solution was stirred at room temperature under hydrogen gas (1 atm.) in the presence of 0.60 g of 10% palladium on carbon until the reaction was complete as determined by reverse-phase HPLC. The mixture was filtered through celite, and the filtrate was concentrated under vacuum. The residue was dissolved in ethyl acetate, and an excess of 4 N hydrogen chloride in dioxane was added. The resulting precipitate was recovered by filtration and dried under vacuum to afford 4.5 g of 2. Mass spec.: m/e 505 $(M+H)^+$.

Step 2: A mixture of 0.54 g (1.0 mmol) of 2, 0.34 g (1.1 mmol) of 3, 0.49 g (1.3 mmol) of HATU, 0.58 mL (3.3 mmol) of diisopropylethylamine, and 10 mL of dimethylformamide was stirred at room temperature for 2 hours. The mixture then was diluted with ethyl acetate. This solution was washed with water, 8% aqueous citric acid solution, 5% aqueous potassium carbonate solution, and brine, dried over anhydrous sodium sulfate, filtered, and concentrated. Column chromatography on silica gel (elution: 30% ethyl acetate/methylene chloride provided 0.65 g of 4.

Step 3: To a solution of 0.65 g of 4 in 10 mL of ethyl acetate at room temperature was added 15 mL of 4 N hydrogen chloride in dioxane, and the reaction mixture was stirred at room temperature for 1 hour. The resulting mixture was diluted with diethyl ether, and the precipitate was recovered by filtration, washed with diethyl ether, and dried under vacuum to afford 0.50 g of Example 1 as its hydrochloride salt. High-resolution mass spec.: calc'd for $C_{37}H_{51}FN_5O_5S$ $(M+H)^+$: 696.3595; found: 696.3598.

Preparation of N-Boc-N-[1-(3-fluorophenyl)-1-cyclopropyl]glycine (3)

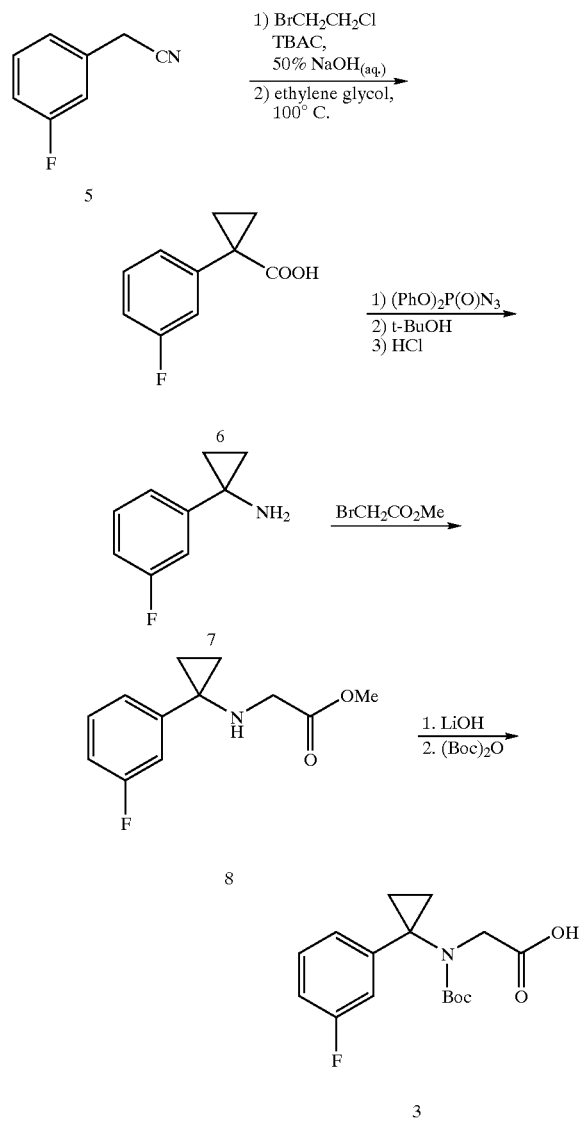

Step 1: To a mixture of 5.8 mL (50 mmol) of 3-fluorophenylacetonitrile(5), 8.3 mL (100 mmol) of 1-bromo-2-chloroethane, and 0.23 g (1.0 mmol) of benzyltriethylammonium chloride was added 28 mL of 50% aqueous sodium hydroxide solution, and the resulting mixture was stirred at 40° C. for 3 hours [M. Fedorynski and A. Jonczyk Org. Prep. Proc. Intl. (1995) 27, 355–359]. At this point 25 mL of ethylene glycol was added, and the mixture then was stirred at 100° C. for another 20 hours. After cooling to room temperature, the reaction mixture was diluted with water and then washed with ethyl acetate. The aqueous phase was adjusted to pH 2 employing hydrochloric acid and then extracted with diethyl ether. The combined extracts were washed with water and brine, dried over anhydrous sodium sulfate, filtered, and concentrated to provide 8.1 g of 1-(3-fluorophenyl)cyclopropane-1-carboxylic acid(6). NMR (300 MHz, DMSO-$d_6$): δ 12.41 (br s, 1 H), 7.37–7.29 (m, 1 H), 7.18–7.03 (m, 3 H), 1.45 (d of d, 2 H), 1.17 (d of d, 2 H).

Step 2: To a solution of 8.0 g (45 mmol) of 1-(3-fluorophenyl)cyclopropane-1-carboxylic acid(6) in 250 mL of toluene at room temperature was added 6.9 mL (150 mmol) of triethylamine followed by 9.7 mL (45 mmol) of diphenylphosphoryl azide. The resulting mixture was stirred at room temperature for 0.5 hour, heated slowly to reflux over 0.5 hour, and then heated at reflux for 2 hours. The mixture was allowed to cooled to 40° C., 25 mL of tert-butanol was added, and the resulting mixture was heated at reflux for another 20 hours. After cooling the mixture was concentrated under vacuum, and the residue was dissolved in diethyl ether. This solution was washed with saturated aqueous sodium bicarbonate solution, water, and brine, dried over anhydrous sodium sulfate, filtered, and concentrated. The residue was dissolved in hot hexane, and the solution was filtered. The filtrate then was concentrated under vacuum to afford 11 g of product.

Step 3: To the product of step 2 in 10 mL of diethyl ether at room temperature was added 50 mL of 4 N hydrogen chloride in dioxane. The solution then was stirred at room temperature for 2 hours. The resulting suspension was filtered, and the solids were washed with diethyl ether and then dried to furnish 6.5 g of 1-(3-fluorophenyl)-1-cyclopropylamine(7) as its hydrochloride salt. NMR (300 MHz, DMSO-$d_6$): δ 9.02 (br s, 3 H), 7.46 (m, 1 H), 7.27 (m, 2 H), 7.19 (t of d, 1 H), 1.42 (m, 2 H), 1.25 (m, 2 H).

Step 4: To a mixture of 3.76 g (20 mmol) of 1-(3-fluorophenyl)-1-cyclopropylamine hydrochloride(7) and 6.2 g (45 mmol) of potassium carbonate in 60 mL of acetonitrile and 10 mL of water at room temperature was added slowly 1.90 mL (20 mmol) of methyl bromoacetate. The reaction mixture was stirred at room temperature for 70 hours and then filtered. The filtrate was concentrated under vacuum, and the residue was dissolve in ethyl acetate. This solution was washed with saturated aqueous sodium bicarbonate solution, water, and brine, dried over anhydrous sodium sulfate, filtered, and concentrated. Column chromatography on silica gel (elution: 10% ethyl acetate/methylene chloride) provided 3.3 g of N-[1-(3-fluorophenyl)-1-cyclopropyl]glycine, methyl ester(8). NMR (300 MHz, CDCl$_3$): δ 7.27 (m, 1 H), 7.06 (d of d, 1 H), 7.00 (d of t, 1 H), 6.91 (t of d, 1 H), 3.66 (s, 3 H), 3.38 (s, 2 H), 1.07 (m, 2 H), 0.94 (m, 2 H).

Step 5: To a solution of 3.3 g (14.8 mmol) of N-[1-(3-fluorophenyl)-1-cyclopropyl]glycine, methyl ester(8) in 75 mL of tetrahydrofuran and 15 mL of water at room temperature was added 1.26 g (30 mmol) of lithium hydroxide monohydrate, and the resulting mixture was stirred at room temperature for 3 hours. At this point 4.8 g (22 mmol) of di-tert-butyl dicarbonate was added, and the reaction mixture was stirred at room temperature for another 70 hours. The mixture was concentrated under vacuum, and the residue was dissolved in 1 N aqueous sodium hydroxide solution, and the resulting solution was washed with diethyl ether. The aqueous phase was cooled to 0° C., adjusted to ~pH 4 by the addition of hydrochloric acid, and extracted with diethyl ether. The combined extracts were washed with 8% aqueous citric acid solution, water, and brine, dried over anhydrous sodium sulfate, filtered, and concentrated. Recrystallization of the crude product from diethyl ether/hexane furnished 4.25 g of N-Boc-N-[1-(3-fluorophenyl)-1-cyclopropyl]glycine(3). NMR (300 MHz, DMSO-$d_6$): δ 12.58 (br s, 1 H), 7.32 (m, 1 H), 6.96 (m, 3H), 3.93 (m, 2 H), 1.40–1.24 (m, 13 H).

Preparation of Compound 1

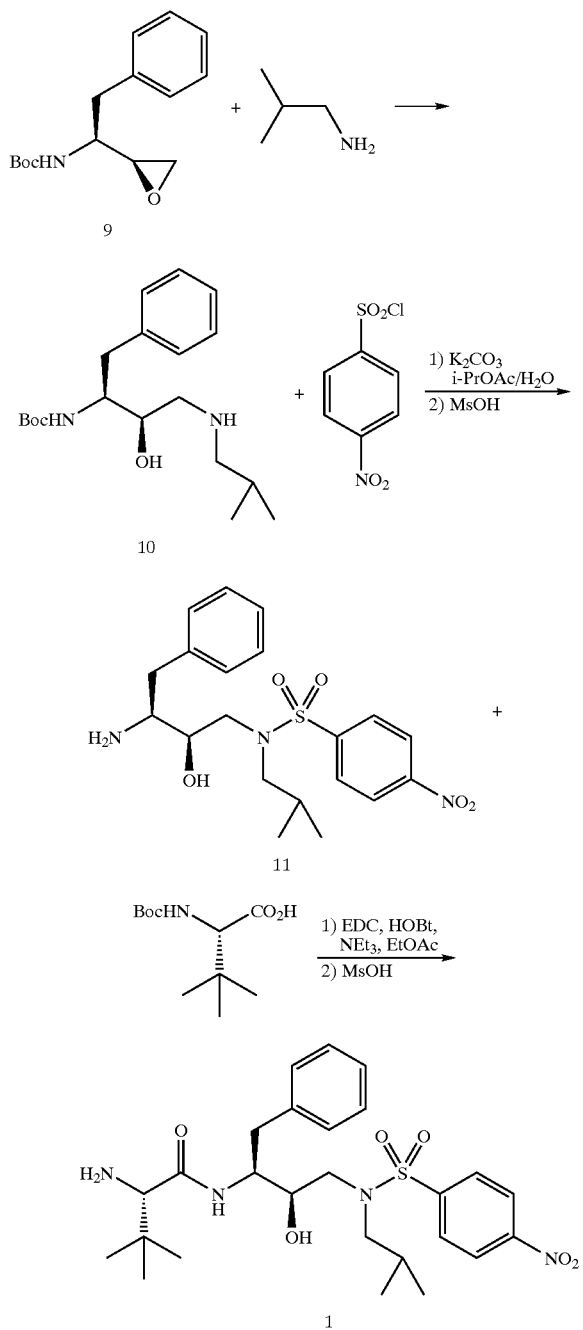

Step 1: To a solution of 1000 mL of isobutylamine and 1000 mL of isopropanol at room temperature was added 500 g of the commercially-available epoxide(9), and the resulting mixture was heated to reflux for 1 hour. After cooling, the mixture was concentrated under vacuum, and the residue was triturated with 1000 mL of heptane. The resulting precipitate was recovered by filtration, washed with heptane, and dried to provide 625 g of the aminoalcohol (10).

Step 2: To a solution of 100 g (300 mmol) of aminoalcohol (10) in 500 mL of isopropyl acetate was added a solution of 83 g (600 mmol) of potassium carbonate in 500 mL of water. The two-phase mixture was vigorously stirred and heated to 50° C., and a solution of 69 g (312 mmol) of 4-nitrobenzenesulfonyl chloride in 200 mL of isopropyl acetate then was added, while the reaction mixture was maintained at 50° C. Finally, the mixture was stirred at 50° C. for another 0.25 hour. After cooling, the phases were separated, and the organic phase was washed with water and brine, dried over anhydrous sodium sulfate, and filtered. The resulting solution was heated to reflux (~85° C.), and 34.3 g (360 mmol) of methanesulfonic acid was added dropwise over 0.5 hour. The mixture was heated at reflux for another 0.5 hour and then allowed to cool to room temperature. The resulting precipitate was recovered by filtration, washed with isopropyl acetate, and dried to afford 140 g of sulfonamide(11) as its methanesulfonate salt. Mass spec.: m/e 422 (M+H)$^+$.

Step 3: To a suspension of 60 g (116 mmol) of the product of step 2, 29.4 g (128 mmol) of N-Boc-L-tert-leucine, and 19.8 g (150 mmol) of 1-hydroxybenzotriazole in 540 mL of ethyl acetate at room temperature was added 74 mL (382 mmol) of triethylamine followed by 26.4 g (139 mmol) of 1-(3-dimethylaminopropyl)-3-ethylcarbodiimide hydrochloride. The resulting mixture was stirred at 40° C. for 2.5 hours. After cooling to room temperature the mixture was diluted with ethyl acetate. This solution was washed with 5% aqueous potassium carbonate solution, water, 8% aqueous citric acid solution, water, and brine, dried over anhydrous sodium sulfate, filtered, and concentrated. The residue was dissolved in 900 mL of ethyl acetate. To this solution was added 7.40 g (150 mmol) of methanesulfonic acid, and the mixture was heated at reflux for 4 hours. After cooling, the suspension was filtered, and the recovered solids were washed with ethyl acetate and dried to furnish 65 g of 1 as its methanesulfonate salt. Mass spec.: m/e 535 (M+H)$^+$.

EXAMPLE 2

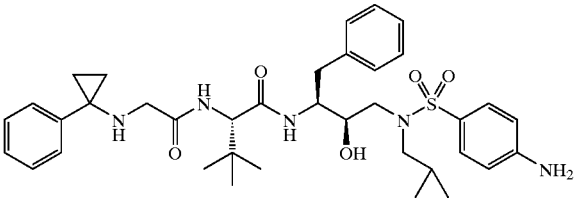

This compound was prepared as described for Example 1 employing 1-phenylcyclopropane-1-carboxylic acid as starting material. High-resolution mass spec.: calc'd for $C_{37}H_{52}N_5O_5S$ (M+H)$^+$: 678.3689; found: 678.3669.

EXAMPLE 3

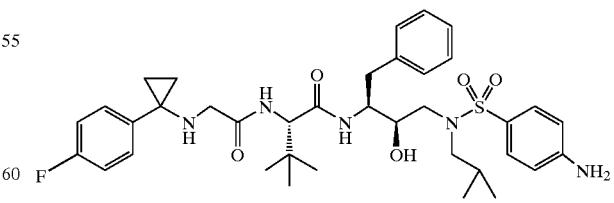

This compound was prepared as described for Example 1 employing 4-fluorophenylacetonitrile as starting material. High-resolution mass spec.: calc'd for $C_{37}H_{51}FN_5O_5S$ (M+H)$^+$: 696.3595; found: 696.3580.

EXAMPLE 4

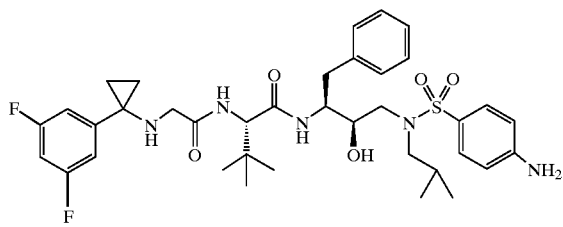

This compound was prepared as described for Example 1 employing 3,5-difluorophenylacetonitrile as starting material. High-resolution mass spec.: calc'd for $C_{37}H_{50}F_2N_5O_5S$ $(M+H)^+$: 714.3501; found: 714.3489.

EXAMPLE 5

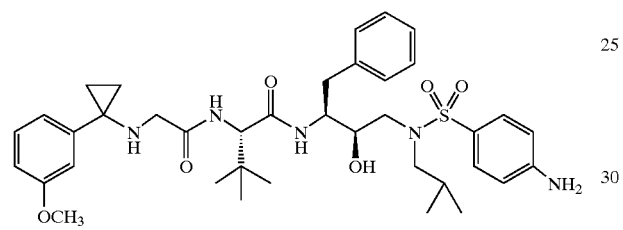

This compound was prepared as described for Example 1 employing 3-methoxyphenylacetonitrile as starting material. High-resolution mass spec.: calc'd for $C_{38}H_{54}N_5O_6S$ $(M+H)^+$: 708.3795; found: 708.3803.

EXAMPLE 6

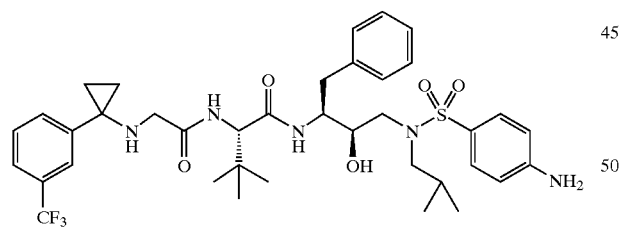

This compound was prepared as described for Example 1 employing 3-trifluoromethylphenylacetonitrile as starting material. High-resolution mass spec.: calc'd for $C_{38}H_{51}F_3N_5O_5S$ $(M+H)^+$: 746.3563; found: 746.3576.

EXAMPLE 7

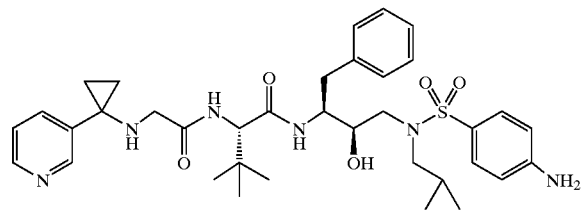

This compound was prepared as described for Example 1 employing 3-pyridylacetonitrile as starting material. High-resolution mass spec.: calc'd for $C_{36}H_{51}N_6O_5S$ $(M+H)^+$: 679.3642; found: 679.3629.

EXAMPLE 8

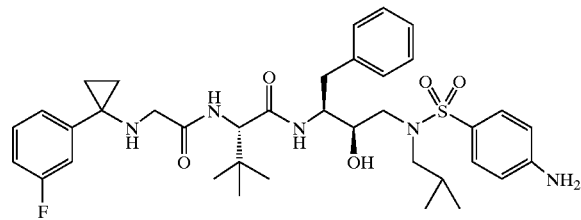

This compound was prepared as described for Example 1 employing N-Boc-L-valine as starting material. High-resolution mass spec.: calc'd for $C_{36}H_{49}FN_5O_5S$ $(M+H)^+$: 682.3438; found: 682.3449.

EXAMPLE 9

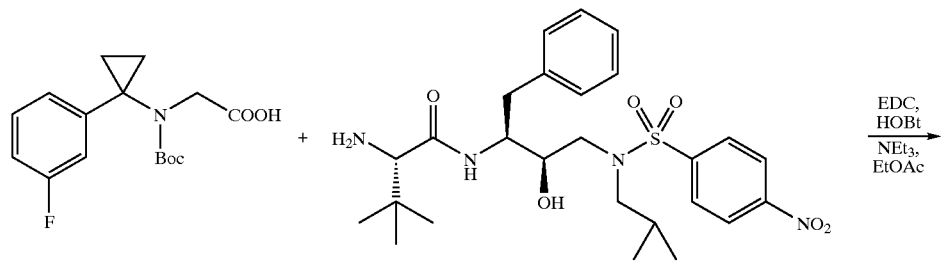

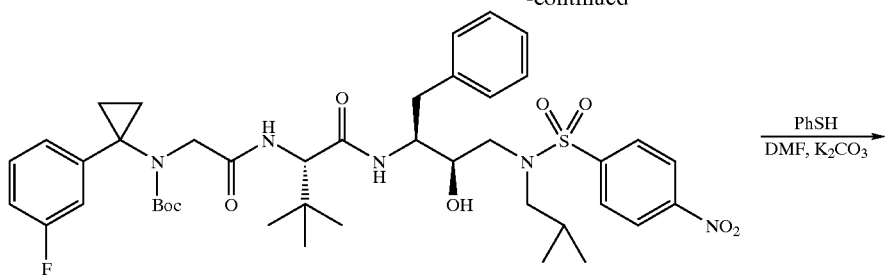

12

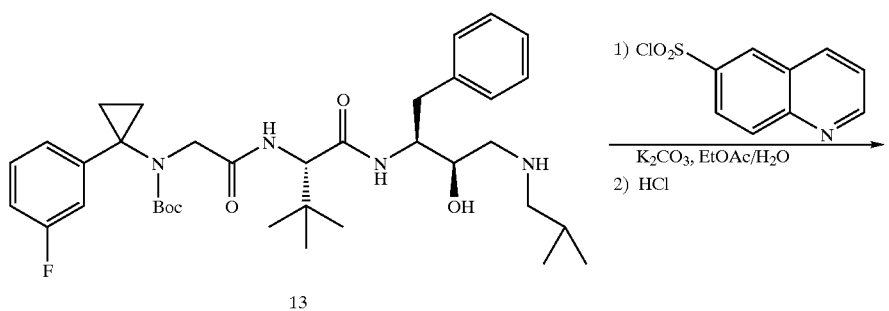

13

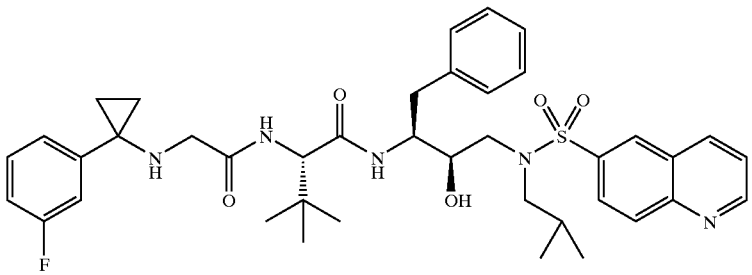

Example 9

Part 1: To a suspension of 3.2 g (5.0 mmol) of 1, 1.7 g (5.5 mmol) of N-Boc-N-[1-(3-fluorophenyl)-1-cyclopropyl] glycine(3), and 0.75 g (5.5 mmol) of 1-hydroxybenzotriazole in 50 mL of ethyl acetate at room temperature was added 2.30 mL (16.5 mmol) of triethylamine followed by 1.2 g (5.5 mmol) of 1-(3-dimethylaminopropyl)-3-ethylcarbodiimide hydrochloride. The resulting mixture was stirred at 40° C. for 2.5 hours. After cooling to room temperature the mixture was diluted with ethyl acetate. This solution was washed with 5% aqueous potassium carbonate solution, water, 8% aqueous citric acid solution, water, and brine, dried over anhydrous sodium sulfate, filtered, and concentrated. Column chromatography on silica gel (elution: 10–20% ethyl acetate/methylene chloride) provided 4.0 g of 12.

Step 2: To a mixture of 4.0 g (4.8 mmol) of 12 and 2.0 g (14.5 mmol) of potassium carbonate in dimethylformamide at room temperature was added 0.77 mL (7.5 mmol) of thiophenol, and the reaction mixture then was stirred at room temperature for 2.5 hours. The mixture was poured into ethyl acetate, and the resulting solution was washed repeatedly with water and then brine, dried over anhydrous sodium sulfate, filtered, and concentrated. Column chromatography on silica gel (elution: 10% methanol/methylene chloride) furnished 2.2 g of 13. Mass spec.: m/e 641 (M+H)$^+$.

Step 3: A mixture of 0.26 g (0.4 mmol) of 13, 0.14 g (0.6 mmol) of quinoline-6-sulfonyl chloride, and 0.55 g (4.0 mmol) of potassium carbonate in 4 mL of ethyl acetate and 4 mL of water was stirred at room temperature for 16 hours. The mixture then was diluted with ethyl acetate, and the resulting solution was washed twice with water and then brine, dried over anhydrous sodium sulfate, filtered, and concentrated. The crude product was employed in the next reaction without further purification.

Step 4: To a solution of the crude product of step 3 in 10 mL of ethyl acetate at room temperature was added 15 mL of 4 N hydrogen chloride in dioxane, and the reaction mixture then was stirred at room temperature for 1 hour. The resulting mixture was diluted by slowly adding 40 mL of diethyl ether. The precipitate was recovered by filtration, washed with diethyl ether, and dried under vacuum to afford 0.2 g of Example 9 as its dihydrochloride salt. High-resolution mass spec.: calc'd for $C_{40}H_{51}FN_5O_5S$ (M+H)$^+$: 732.3595; found: 732.3605.

EXAMPLE 10

31

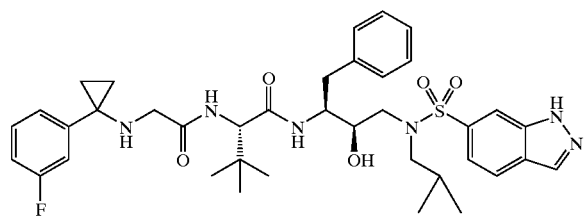

This compound was prepared as described for Example 9 employing indazole-6-sulfonyl chloride as starting material. High-resolution mass spec.: calc'd for $C_{38}H_{50}FN_6O_5S$ (M+H)$^+$: 721.3547; found: 721.3571.

EXAMPLE 11

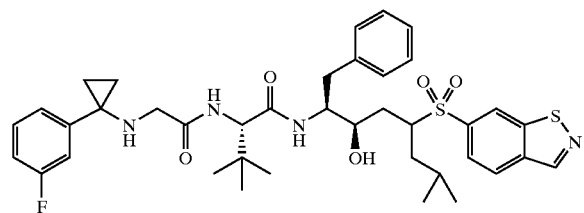

This compound was prepared as described for Example 9 employing benzothiazole-6-sulfonyl chloride as starting material. High-resolution mass spec.: calc'd for $C_{38}H_{49}FN_5O_5S_2$ (M+H)$^+$: 738.3159; found: 738.3156.

EXAMPLE 12

32

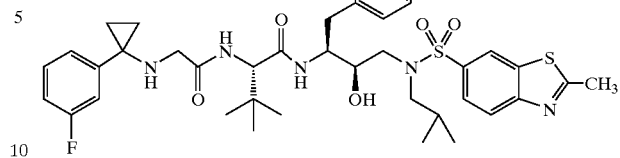

This compound was prepared as described for Example 9 employing 2-methylbenzothiazole-6-sulfonyl chloride as starting material. High-resolution mass spec.: calc'd for $C_{39}H_{51}FN_5O_5S_2$ (M+H)$^+$: 752.3316; found: 752.3339.

EXAMPLE 13

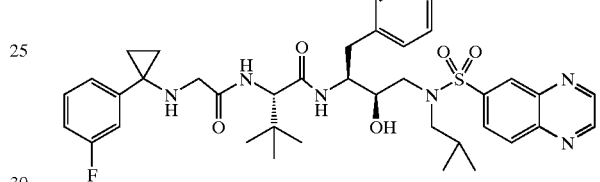

This compound was prepared as described for Example 9 employing quinoxaline-6-sulfonyl chloride as starting material. High-resolution mass spec.: calc'd for $C_{39}H_{50}FN_6O_5S$ (M+H)$^+$: 733.3547; found: 733.3534.

EXAMPLE 14

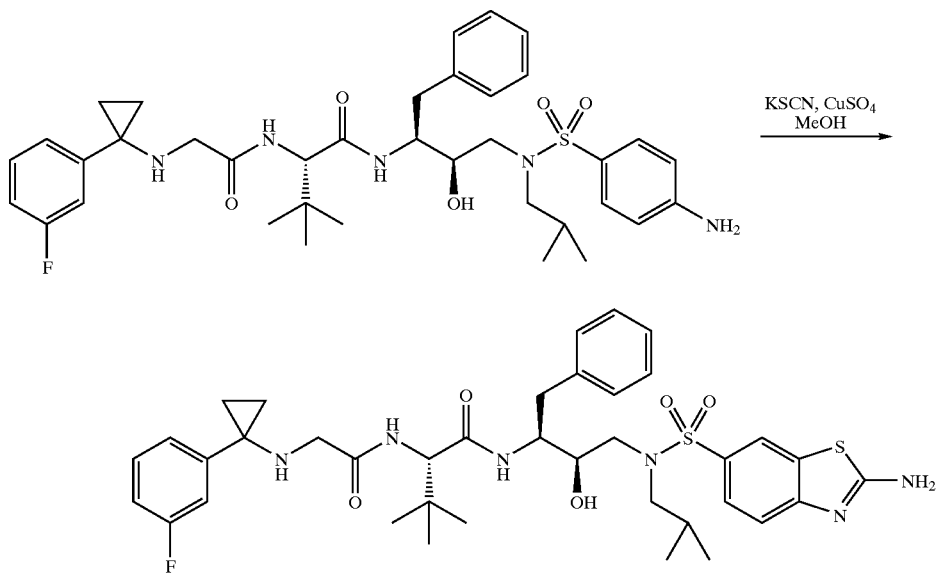

Example 14

A mixture of 0.30 g (0.4 mmol) of Example 1, 1.05 g of potassium thiocyanate, 0.84 g of copper(II)sulfate, and 5 mL of methanol was heated at reflux for 2 hours. After cooling, the mixture was filtered, diluted with 5 mL of water, and heated at reflux for another 1 hour. Finally, the mixture was diluted with 8 mL of ethanol, allowed to cool to room temperature, and filtered. The filtrate was concentrated under vacuum, and the residue was dissolved in ethyl acetate. The organic solution was washed twice with an aqueous ammonium chloride/ammonia buffer followed by brine, dried over anhydrous sodium sulfate, filtered, and concentrated. Column chromatography on silica gel (elution: 2–5% methanol/methylene chloride) provided the pure product as its free-base. This material was dissolved in 5 mL of 1,4-dioxane to which was added excess of 4 N hydrogen chloride in dioxane followed by ~20 mL of diethyl ether. The resulting precipitate was recovered by filtration, washed with diethyl ether, and dried under vacuum to afford Example 14 as its hydrochloride salt. High-resolution mass spec.: calc'd for $C_{38}H_{50}FN_6O_5S_2$ $(M+H)^+$: 753.3268; found: 753.3258.

EXAMPLE 15

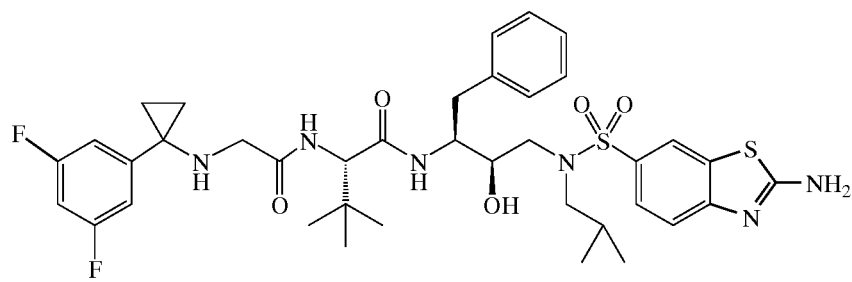

This product was prepared from Example 4 as described for Example 14. High-resolution mass spec.: calc'd for $C_{38}H_{49}F_2N_6O_5S_2$ $(M+H)^+$: 771.3174; found: 771.3173.

EXAMPLE 16

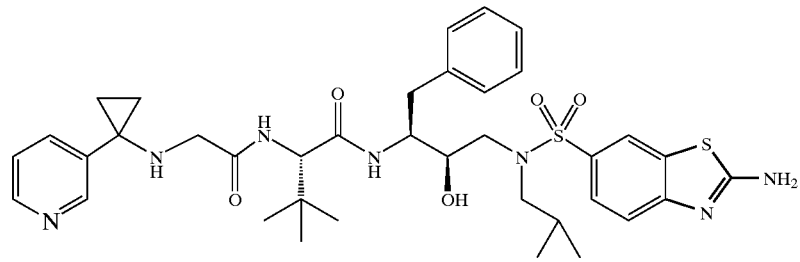

This product was prepared from Example 7 as described for Example 14. High-resolution mass spec.: calc'd for $C_{37}H_{50}N_7O_5S_2$ $(M+H)^+$: 736.3315; found: 736.3304.

EXAMPLE 17

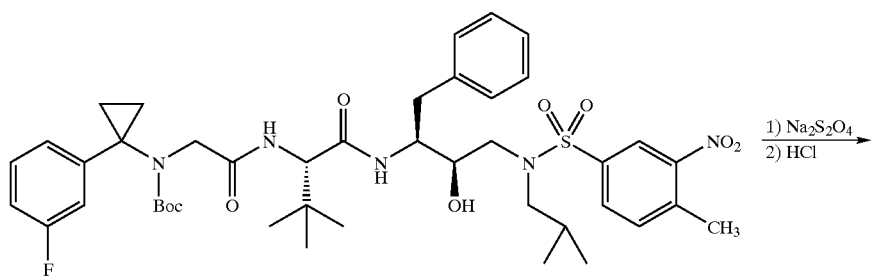

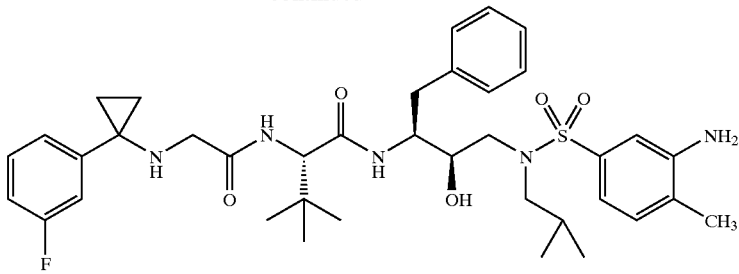

Example 17

Step 1: To a solution of 0.42 g (0.5 mmol) of 14 (prepared as described for Example 9 employing 4-methyl-3-nitrobenzenesulfonyl chloride as starting material) in 10 mL of ethanol and 2 mL of conc. aqueous ammonium hydroxide at room temperature was added a solution of 0.70 g (4 mmol) of sodium dithionite in 4 mL of water, and the reaction mixture then was stirred at room temperature for 18 hours. The resulting mixture was diluted with water and then extracted with ethyl acetate. The combined extracts were washed with water and brine, dried over anhydrous sodium sulfate, filtered, and concentrated. Column chromatography on silica gel (elution: 30% ethyl acetate/methylene chloride) afforded 0.24 g of product.

Step 2: A solution of 0.24 g of the product from step 1 in 10 mL of ethyl acetate and 15 mL of 4 N hydrogen chloride was stirred at room temperature for 1 hour. The mixture then was diluted by slowly adding 40 mL of diethyl ether. The resulting precipitate was recovered by filtration, washed with diethyl ether, and dried under vacuum to provide 0.12 g of Example 17 as its hydrochloride salt. High-resolution mass spec.: calc'd for $C_{38}H_{53}FN_5O_5S$ (M+H)$^+$: 710.3751; found: 710.3753.

EXAMPLE 18

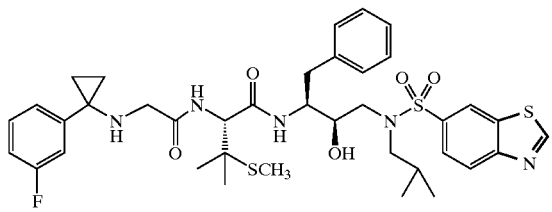

This compound was prepared as described for Examples 1 and 9 employing N-Boc-S-methylpenicillamine and benzothiazole-6-sulfonyl chloride as starting materials. High-resolution mass spec.: calc'd for $C_{38}H_{49}FN_5O_5S_3$ (M+H)$^+$: 770.2880; found: 770.2858.

Preparation of N-Boc-S-methylpenicillamine

To a solution of 5.09 g (34.1 mmol) of penicillamine and 12 mL of 6 N aqueous sodium hydroxide solution in 75 mL of 1,4-dioxane and 25 mL of water at 0° C. was added 2.35 mL (37.6 mmol) of iodomethane. The reaction mixture was stirred at 0° C. for 3 hours followed by 2 hours at room temperature. The mixture was returned to 0° C., and 8.7 g (40.0 mmol) of di-tert-butyl dicarbonate was added slowly. The resulting mixture was stirred at 0° C. for 1 hour followed by 14 hours at room temperature. The mixture then was concentrated under vacuum, and the residue was diluted with water. This aqueous phase was washed with diethyl ether, adjusted to ~pH 3 employing hydrochloric acid, and then extracted with ethyl acetate. The combined extracts were washed with brine, dried over anhydrous sodium sulfate, filtered, and concentrated to afford 7.0 g of the desired aminoacid.

EXAMPLE 19

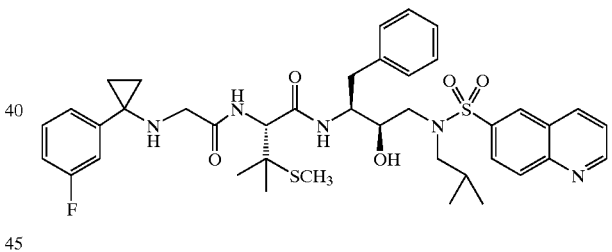

This compound was prepared as described for Examples 1 and 9 employing N-Boc-S-methylpenicillamine and quinoline-6-sulfonyl chloride as starting materials. High-resolution mass spec.: calc'd for $C_{40}H_{51}FN_5O_5S_2$ (M+H)$^+$: 764.3316; found: 764.3328.

EXAMPLE 20

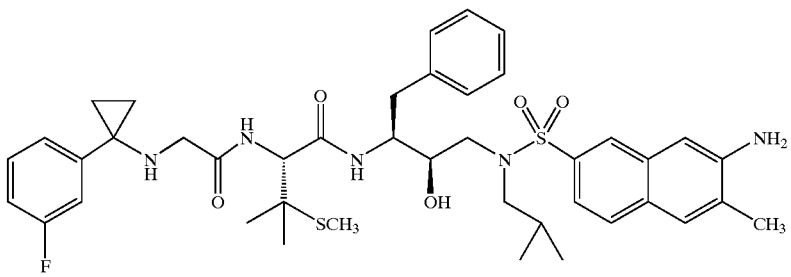

This compound was prepared as described for Examples 1, 9, and 17 employing N-Boc-S-methylpenicillamine and 4-methyl-3-nitrobenzenesulfonyl chloride as starting materials. High-resolution mass spec.: calc'd for $C_{38}H_{53}FN_5O_5S_2$ (M+H)$^+$: 742.3472; found: 742.3488.

EXAMPLE 21

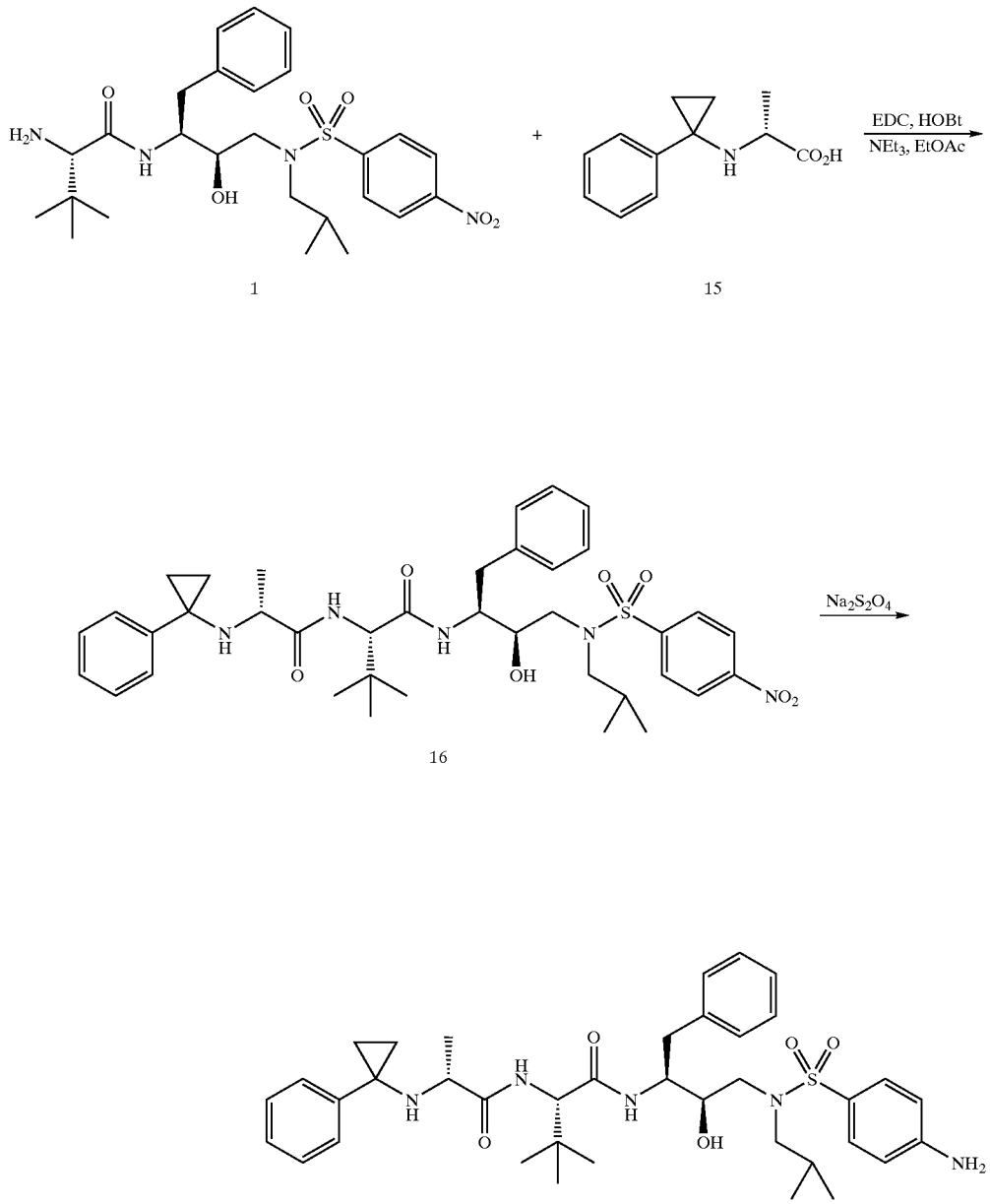

Example 21 with water, 8% aqueous citric acid solution, water, 5% aqueous potassium carbonate solution, water, and brine, dried over anhydrous sodium sulfate, filtered, and concentrated. Column chromatography on silica gel (elution: 10–30% ethyl acetate/methylene) furnished 3.25 g of 16.

Step 2: To a solution of 0.72 g of 16 in 35 mL of ethanol and 5 mL of conc. aqueous ammonium hydroxide at room Step 1: To a mixture of 7.11 g (11.3 mmol) of 1, 3.00 g (12.4 mmol) of N-(1-phenyl-1-cyclopropyl)-D-alanine hydrochloride(15), and 1.68 g (12.4 mmol) of 1-hydroxybenzotriazole in 100 mL of ethyl acetate at room temperature was added 6.30 mL (45 mmol) of triethylamine followed by 2.60 g (13.5 mmol) of 1-(3-dimethylaminopropyl)-3-ethylcarbodiimide hydrochloride. The resulting mixture was stirred at 40–45° C. for 4 hours. After cooling to room temperature the mixture was washed temperature was added a solution of 1.00 g of 85% sodium dithionite in 20 mL of water. The reaction mixture was stirred at room temperature for 20 hours. The mixture then was filtered, and the filtrate was diluted with water, adjusted to pH<1 with conc. hydrochloric acid, and stirred at room temperature for 0.5 hour. The mixture was adjusted to ~pH 12 with 50% aqueous sodium hydroxide solution and then extracted with ethyl acetate. The combined extracts were washed with water and brine, dried over anhydrous sodium sulfate, filtered, and concentrated. The original crude product was found to be a mixture of the desired product and its SO$_3$-complex. To disrupt this complex the residue was dissolved in a mixture of 20 mL of acetonitrile and 20 mL of 1 N hydrochloric acid, and the solution was stirred at room temperature for 72 hours. The solution was adjusted to ~pH 9 with 1 N aqueous sodium hydroxide solution and then extracted with ethyl acetate. The combined extracts were washed with water and brine, dried over anhydrous sodium sulfate, filtered, and concentrated. Column chromatography on silica gel (elution: 5% methanol/methylene chloride) furnished the product as its free-base. This material was dissolved in 5 mL of 1,4-dioxane. To this solution was added a slight excess of 4 N hydrogen chloride in dioxane followed by the slow addition of ~20 mL of diethyl ether. The resulting precipitate was recovered by filtration, washed with diethyl ether, and dried under vacuum to afford 0.46 g of Example 21 as its hydrochloride salt. High-resolution mass spec.: calc'd for $C_{38}H_{54}N_5O_5S$ (M+H)$^+$: 692.3846; found: 692.3861.

Preparation of N-(1-phenyl-1-cyclopropyl)-D-alanine hydrochloride

Step 1: To a solution of 6.42 g (48 mmol) of 1-phenyl-cyclopropylamine [obtained from 1-phenylcyclopropane-1-carboxylic acid through a Curtius rearrangement as described in Example 1] in 50 mL of methylene chloride at room temperature was added 4.02 g (16 mmol) of ethyl O-trifluoromethanesulfonyl-L-lactate, and the reaction mixture was stirred at room temperature for 18 hours. The mixture was filtered, and the filtrate was washed with water and brine, dried over anhydrous sodium sulfate, filtered, and concentrated. Column chromatography on silica gel (elution: 5% ethyl acetate/methylene chloride) furnished 2.65 g of N-(1-phenyl-1-cyclopropyl)-D-alanine, ethyl ester. NMR (300 MHz, CDCl$_3$) δ 7.36–7.18 (m, 5 H), 3.94 (quart., 2 H), 3.36 (quart., 1 H), 1.22 (d, 3 H), 1.17 (t, 3 H), 1.08–0.78 (m, 4 H).

Step 2: To a solution of 2.65 g of N-(1-phenyl-1-cyclopropyl)-D-alanine, ethyl ester in 40 mL of ethanol at room temperature was added an excess of 50% aqueous sodium hydroxide solution, and the reaction mixture was stirred at room temperature for 1 hour. The mixture was diluted with water, adjusted to pH 2–3 with conc. hydrochloric acid, and concentrated to dryness under vacuum. The resulting solids were suspended in brine, and this aqueous mixture was extracted with 1:4 isopropanol/chloroform. The combined extracts were dried over anhydrous sodium sulfate, filtered, and concentrated to afford 3.15 g of N-(1-phenyl-1-cyclopropyl)-D-alanine hydrochloride(15).

EXAMPLE 22

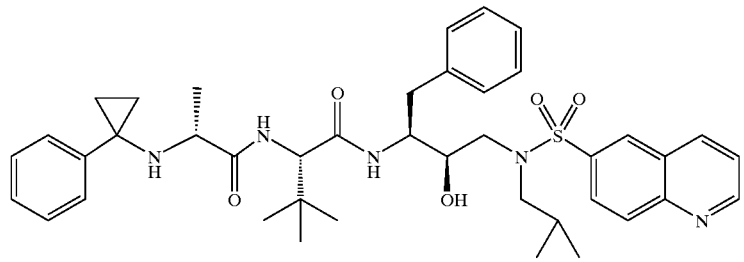

This compound was prepared as described for Example 9 employing 16 from Example 21 and quinoline-6-sulfonyl chloride as starting materials. High-resolution mass spec.: calc'd for $C_{41}H_{54}N_5O_5S$ (M+H)$^+$: 728.3846; found: 728.3869.

EXAMPLE 23

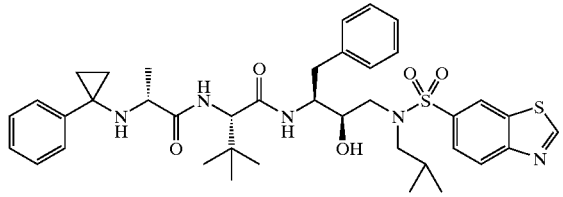

This compound was prepared as described for Example 9 employing 16 from Example 21 and benzothiazole-6-sulfonyl chloride as starting materials. High-resolution mass spec.: calc'd for $C_{39}H_{52}N_5O_5S_2$ (M+H)$^+$: 734.3410; found: 734.3423.

EXAMPLE 24

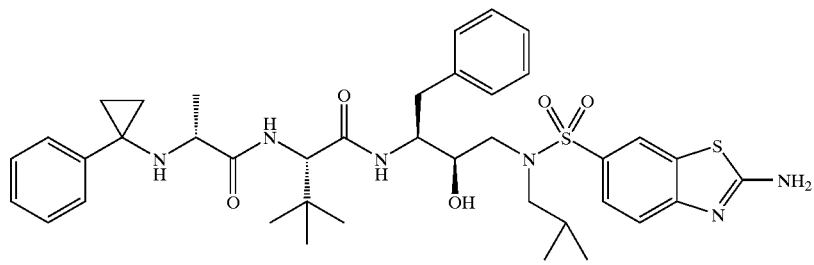

This product was prepared from Example 21 as described for Example 14. High-resolution mass spec.: calc'd for $C_{39}H_{53}N_6O_5S_2$ (M+H)$^+$: 749.3519; found: 749.3503.

What is claimed is:

1. A compound of Formula (I)

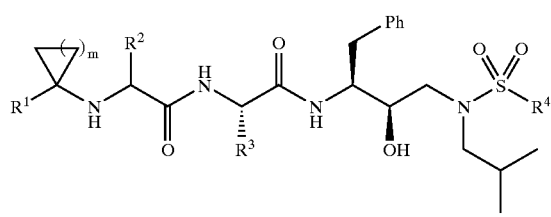
(I)

wherein:

R¹ is phenyl, pyridinyl, pyrimidinyl, pyrazinyl, or pyridazinyl, and is unsubstituted or substituted with 1-2 substituents selected from the group consisting of halogen, $C_{1-6}$alkyl, trifluoromethyl, $C_{1-6}$alkoxy, trifluoromethoxy, and cyano;

R² is hydrogen or $C_{1-6}$alkyl;

R³ is selected from the group consisting of isopropyl, tert-butyl, sec-butyl, and $C(CH_3)_2SCH_3$;

R⁴ is phenyl, indazolyl, benzothiazolyl, quinolinyl, quinoxalinyl, 2,3-dihydrobenzofuranyl, or 1,3-benzodioxolyl, and is unsubstituted or substituted with 1-2 substituents selected from the group consisting of amino, acetamido, halo, $C_{1-6}$alkyl, trifluoromethyl, $C_{1-6}$alkoxy, trifluoromethoxy, and cyano; and m is 1, 2, 3, or 4;

or a pharmaceutically acceptable salt thereof.

2. A compound of claim 1 wherein R¹ is phenyl, 3-fluorophenyl, 4-fluorophenyl, 3,5-difluorophenyl, 2,4-difluorophenyl, 2,6-difluorophenyl, 3-trifluoromethylphenyl, 3-pyridinyl, or 3-methoxyphenyl.

3. A compound of claim 2 where R¹ is phenyl, 3-fluorophenyl, 4-fluorophenyl, 3,5-difluorophenyl, 3-trifluoromethylphenyl, 3-pyridinyl, or 3-methoxyphenyl.

4. A compound of claim 1 where R² is hydrogen or methyl.

5. A compound according to claim 1 wherein R⁴ is selected from the group consisting of 4-aminophenyl, 3-aminophenyl, 3-amino-4-methylphenyl, 4-methoxyphenyl, 6-benzothiazolyl, 2-amino-6-benzothiazolyl, 2-acetamido-6-benzothiazolyl, 2-methyl-6-benzothiazolyl, 7-benzothiazolyl, 2-amino-7-benzothiazolyl, 2-acetamido-7-benzothiazolyl, 2-methyl-7-benzothiazolyl, 2,3-dihydrobenzofuran-5-yl, 2,3-benzodioxl-5-yl, 6-indazolyl, 6-quinolinyl, and 6-quinoxalinyl.

6. A compound according to claim 5 wherein R⁴ is selected from the group consisting of 4-aminophenyl, 3-amino-4-methylphenyl, 6-indazolyl, 6-benzothiazolyl, 2-methyl-6-benzothiazolyl, 2-amino-6-benzothiazolyl, 6-quinolinyl, and 6-quinoxalinyl.

7. A compound of claim 1 with the stereochemistry as designated in Formula Ia.

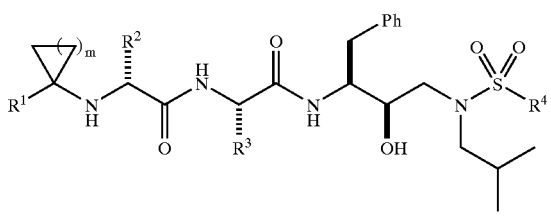
Ia

8. A compound according to claim 1 wherein m is 1.

9. A compound according to claim 1 selected from the group consisting of

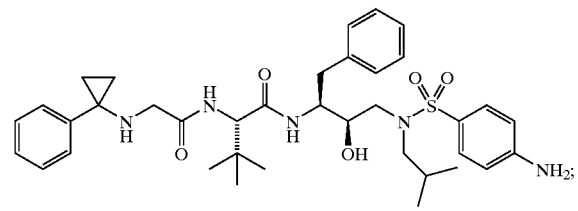

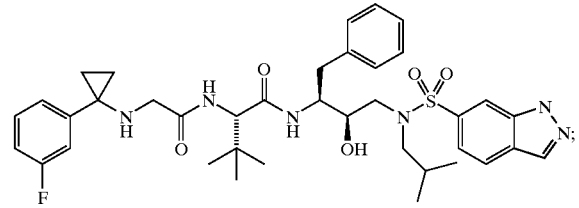

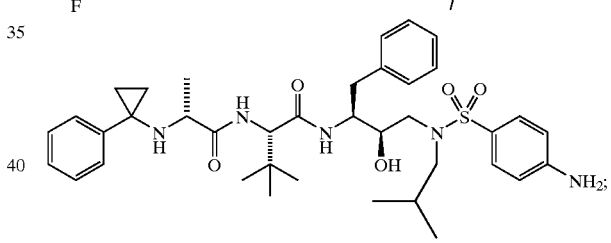

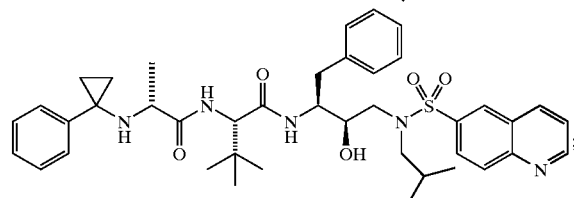

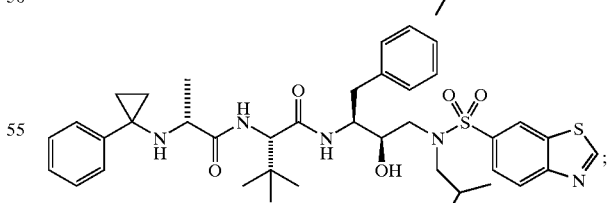

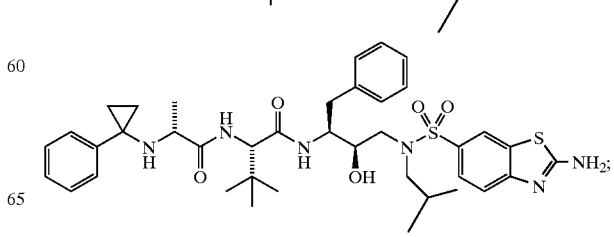

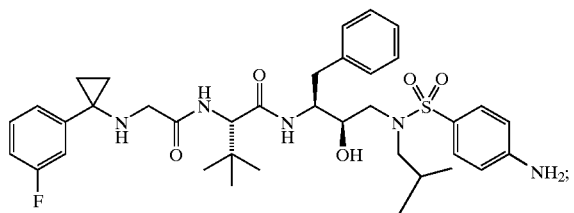
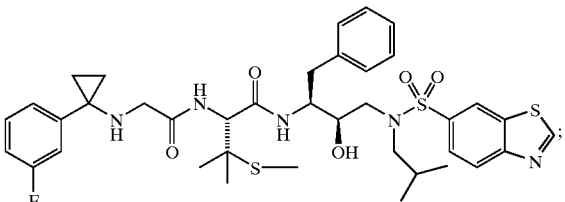
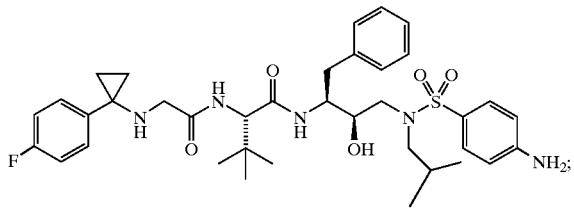
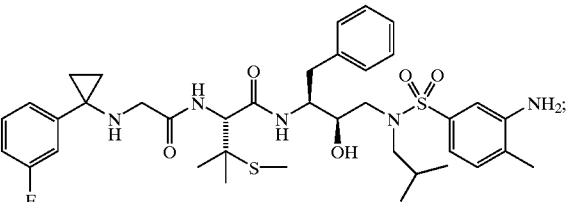
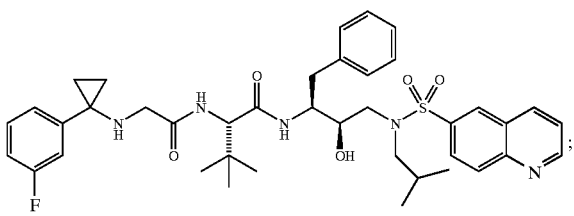
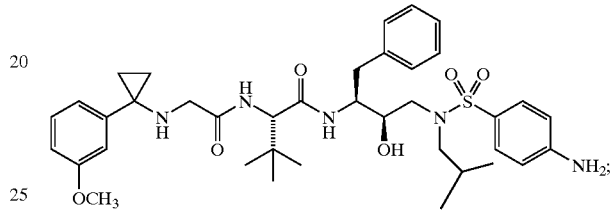
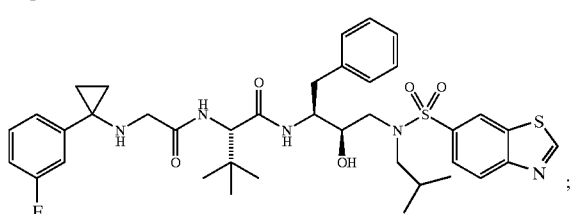
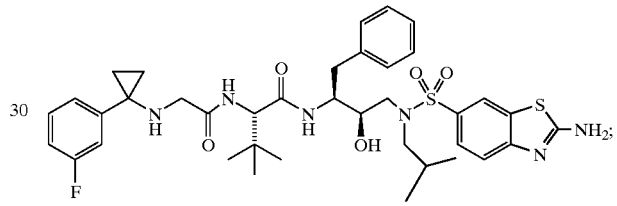
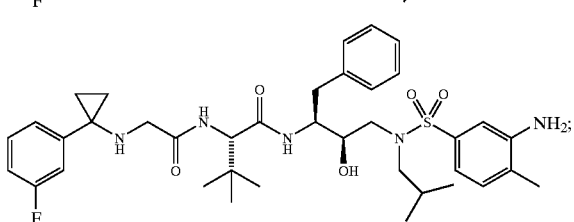
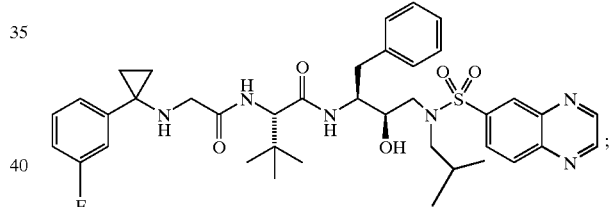
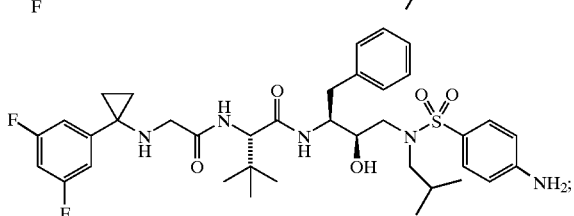
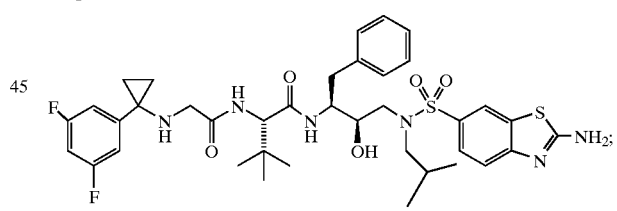
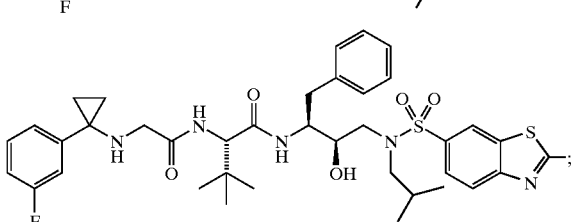
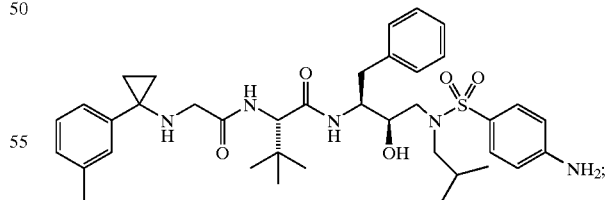
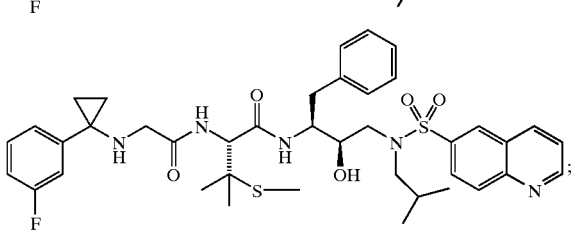
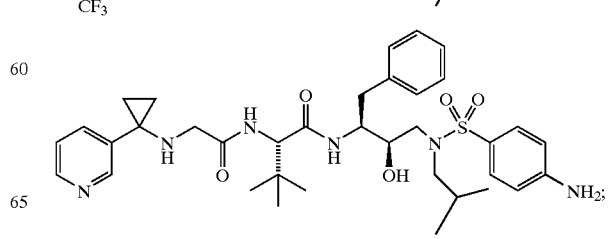

-continued

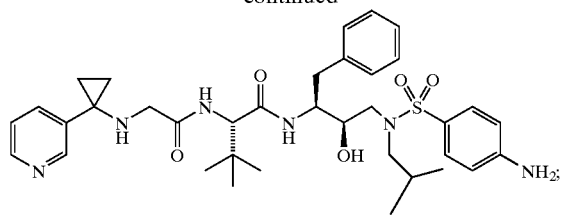

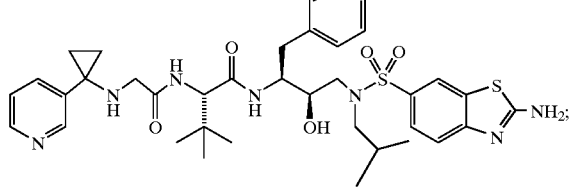

and

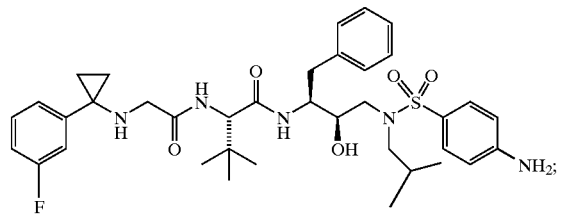

or a pharmaceutically acceptable salt thereof.

10. A pharmaceutical composition comprising a therapeutically effective amount of a compound of claim 1 and a pharmaceutically acceptable carrier.

11. A method for inhibiting HIV protease comprising administering a therapeutically effective amount of a compound of claim 1 to a patient in need of such treatment.

12. A method for treating HIV infection comprising administering a therapeutically effective amount of a compound of claim 1 to a patient in need of such treatment.

13. The method of claim 12 comprising co-administering a therapeutic amount of an HIV reverse transcriptase inhibitor, an HIV protease inhibitor, or a combination thereof.

14. A method for treating AIDS or ARC comprising administering a therapeutically effective amount of a compound of claim 1 to a patient in need of such treatment.

15. The method of claim 14 comprising co-administering a therapeutic amount of an HIV reverse transcriptase inhibitor, an HIV protease inhibitor, or a combination thereof.

* * * * *